United States Patent
Ni et al.

(10) Patent No.: US 12,042,271 B2
(45) Date of Patent: Jul. 23, 2024

(54) PARAMETRIC SYSTEM FOR TESTING CAPABILITY OF AUDITORY SPATIAL POSITIONING AND METHOD OF PROVIDING PARAMETRIC MINIMUM AUDIBLE ANGLE

(71) Applicant: TIANJIN UNIVERSITY, Tianjin (CN)

(72) Inventors: Guangjian Ni, Tianjin (CN); Zihao Xu, Tianjin (CN); Dong Ming, Tianjin (CN); Baolu Liu, Tianjin (CN); Haiyu Zhang, Tianjin (CN); Qi Zheng, Tianjin (CN); Jia Pang, Tianjin (CN)

(73) Assignee: TIANJIN UNIVERSITY, Tianjin (CN)

( * ) Notice: Subject to any disclaimer, the term of this patent is extended or adjusted under 35 U.S.C. 154(b) by 453 days.

(21) Appl. No.: 17/439,331

(22) PCT Filed: Apr. 18, 2020

(86) PCT No.: PCT/CN2020/085480
§ 371 (c)(1),
(2) Date: Sep. 14, 2021

(87) PCT Pub. No.: WO2020/221034
PCT Pub. Date: Nov. 5, 2020

(65) Prior Publication Data
US 2022/0175277 A1    Jun. 9, 2022

(30) Foreign Application Priority Data

Apr. 29, 2019    (CN) .......................... 201910356161.7

(51) Int. Cl.
*H04R 29/00*    (2006.01)
*A61B 5/12*    (2006.01)
*H04S 7/00*    (2006.01)

(52) U.S. Cl.
CPC .............. *A61B 5/123* (2013.01); *H04S 7/304* (2013.01); *H04S 2400/11* (2013.01)

(58) Field of Classification Search
CPC ................................ A61B 5/123; H04S 7/304
See application file for complete search history.

(56) References Cited

U.S. PATENT DOCUMENTS

2004/0254753 A1* 12/2004 Bengtsson ............... A61B 5/12
73/1.82
2018/0136899 A1* 5/2018 Risberg ................... G06F 3/165

FOREIGN PATENT DOCUMENTS

| CN | 102871666 A | 1/2013 |
| CN | 103989481 A | 8/2014 |

(Continued)

OTHER PUBLICATIONS

International Search Report of PCT/CN2020/085480.
Written Opinion of PCT/CN2020/085480.

*Primary Examiner* — Simon King

(57) ABSTRACT

The invention discloses a parametric system for testing a capability of auditory spatial positioning and a method of providing a parametric minimum audible angle. The system includes: an host computer system calculating spatial movement data and communicating with a slave computer; a spatial movement system realizing control of any spatial position through circumferential movement, radial movement and vertical movement; a real-time three-dimensional display system built into the host computer system; an audio system randomly generates a type of audio data of a sound source and a sound source with equal-difference decibels; and a test system for matching human spatial positioning results to sound source spatial data and providing an objective evaluation. The invention further provides a method of (Continued)

providing a parametric minimum audible angle for a capability of auditory spatial positioning, the invention improves the control accuracy.

9 Claims, 3 Drawing Sheets

(56) References Cited

FOREIGN PATENT DOCUMENTS

| | | |
|---|---|---|
| CN | 104352243 A | 2/2015 |
| CN | 109299489 A | 2/2019 |
| CN | 109998553 A | 7/2019 |
| KR | 100697109 B1 | 3/2007 |
| WO | WO2017203028 A1 | 11/2017 |

* cited by examiner

PARAMETRIC SYSTEM FOR TESTING CAPABILITY OF AUDITORY SPATIAL POSITIONING AND METHOD OF PROVIDING PARAMETRIC MINIMUM AUDIBLE ANGLE

CROSS-REFERENCE TO RELATED APPLICATIONS

This application is a national stage application of PCT/CN2020/085480. This application claims priorities from PCT Application No. PCT/CN2020/085480, filed Apr. 18, 2020, and from the Chinese patent application 2019103561617 filed Apr. 29, 2019, the content of which are incorporated herein in the entirety by reference.

TECHNICAL FIELD

The invention relates to the field of auditory spatial positioning, more particularly, to a parametric system for testing a capability of auditory spatial positioning, the system relating to the human capability of auditory spatial identification of sound sources in a three-dimensional space.

BACKGROUND OF THE PRESENT INVENTION

Identification of the position of a sound source is one of the most important functions of the human ear. Either one ear or both ears are capable of positioning. Monoaural (with one ear) positioning functions in a way that an auditory effect is caused by the reflection of incident sound waves on various parts of the auricle, which is called the auricle effect. Binaural (with both ears) positioning relies on two clues, i.e., a difference in the time when the sound reaches both ears and a difference in the intensity of the sound reaching both ears, to position the sound source. Monoaural positioning plays its role mainly in the vertical direction, while binaural positioning functions mainly in the horizontal direction. The sound waves emitted from the sound source propagate to both ears, and then input information on the cochlear nerves on both sides is generated through the sensation of the cochlea of both ears, which is followed by the analysis and synthesis in the central system, and subject to the necessary collaboration of the auditory areas of the brain on both sides, the direction from which the sound comes may be identified. Only when there is a difference in the auditory senses of the two ears, the brain nerves can identify the spatial position of the sound source based on these differences. Differences in sound level, time, phase and timbre, and Haas effect as well as De Poher effect of the sound waves emitted from the sound source and reaching both ears provide a basis for the identification of the position of the sound source. When positioning a low-frequency (0.5-2 kHz) sound source, people are sensitive to the difference in time (difference in phase), the maximum difference in time perceivable by human is 700 ms, and the spatial sound source can be positioned within a spectrum of 10-20 ms; when positioning a high-frequency (4-16 kHz) sound source, people are sensitive to the difference in intensity.

The auditory system matures earlier in the development of a human body, since it starts 3 months before birth, newborns and infants have a capability of position a sound source to a certain extent and can identify whether a sound comes from the left or the right. The capability of young children to identify a sound source in a vertical direction grows over time and shows an increasing correct rate that will reach 1°~2° by the age of 5, almost the same as that of adults. The subjects of the test of sound source positioning include two groups of people, i.e., the newborns and subjects who take normal physical examination, and subjects with hearing disorders. At present, the tests of positioning a sound source for subjects with hearing disorders include three types, that is, those for subjects with unilateral cochlear implantation, those for subjects with bilateral cochlear implantation, and those for subjects with cochlear implant in one ear and a hearing aid in the other ear.

At present, a common tool for the test of positioning a sound source is sound cage. The main technical indicators of a sound cage include: equal distances from each fixed sound source to a center, i.e., a radius of the sound cage, for example, 500 mm; a total of 25 fixed positions of the sound sources, arranged on three transverse sections and four longitudinal sections, with 8 sound sources on each transverse section, and 7 sound sources on each longitudinal section; sound source audios classified as high frequency (3500 Hz), intermediate frequency (1000 Hz), and low frequency (300 Hz); a continuously adjustable volume; 10 to 100 times (ten times per grade) of the test; automatic true/false identification, and real-time display of the identification results; and a keyboard for the subject to input respond, composed of 25 positional keys and indicator lights of states when ready, correct, and false. The device can not only provide sound stimulus in 25 positions equidistant from an auditory axis center, but also digitally display the correct rate of auditory positioning in real time, so it is a common tool for testing the capability of auditory positioning.

However, the common tool for testing the auditory capability of positioning use 25 fixed sound source positions for random sound source tests, which is not enough to provide a more accurate sound source test for any a random spatial position, and the most problematic issue is that it cannot provide the subject with a minimum audible angle to position the sound source.

In summary, it's desirable if an auditory positioning test system can accurately position any random point on a sphere in a three-dimensional space, parametrically control the precise position of the sound source, and provide the subject with a precise minimum audible angle in an auditory space. There has been no relevant research on such a test system.

SUMMARY OF THE PRESENT INVENTION

In view of the defects of the system in the prior art, the present invention provides a parametric system for testing auditory positioning of a random spatial position, and the system provides an accurate parameterization of a minimum audible angle in an auditory space for the subjects. The details are provided as follows.

A parametric system for testing a capability of auditory spatial positioning, including:
  a host computer system, calculating spatial movement data according to a spatial coordinate conversion algorithm based on nonlinear least squares and communicating with a slave computer, and a spatial movement system, realizing precise control of any spatial position through circumferential movement, radial movement and vertical movement;
  a real-time three-dimensional display system, built into the host computer system to reconstruct a three-dimensional model in real time through a system image and feedback real-time movement data of the system on the basis of virtual reality technologies; and an audio system, randomly generating a type of audio data of a sound source and a sound source with equal-difference decibels; and an objective evaluation system for subjects, testing the spatial positioning of the sound source by human ears, selecting spatial point data, matching to real spatial data of the sound source, and providing an objective evaluation.

Wherein, the host computer system is composed of an industrial personal computer, a monitor with a 144 Hz refresh-rate, and a communication cable.

Wherein the industrial personal computer randomly generates a time series and spatial positions of spatial test points of the sound source according to the spatial conversion algorithm on the basis of clinical indicators and physiological parameters of the subjects, caches such data in a data area, and sends the data to a driver of the spatial movement system by following a communication protocol.

The audio system randomly generates optimal sound source audio data in a same number as that of spatial positions on the basis of clinical experience and the physiological parameters of the subjects and matches the sound source audio data randomly one by one to spatial coordinate data, and generated audio signals are randomly and repeatedly played according to a time sequence of coordinate points.

Further, according to the objective evaluation system for subjects, a spatial position of the sound source is selected by a subject on an interface of the real-time three-dimensional display system, the spatial position selected by the subject is tried to match a spatial position in a cache list, and then the objective evaluation system for subjects provides an objective evaluation result of the subject's capability of spatial positioning.

The industrial personal computer arranges coordinates in a data list in such a manner that a spatial mid-point between the subject's ears as a current coordinate origin, converts the coordinates into circumferential movement pulses, radial movement pulses and vertical movement pulses, and temporarily stores these data in a data stack according to a time label.

In a specific implementation, the subject identifies the spatial position according to audio information of the sound source and selects the spatial position of a virtual entity on the subject's monitor, the industrial personal computer matches coordinate information of the spatial position selected by the subject with cache data of a corresponding spatial position in sequence and provides a result whether the subject has correctly identified the spatial position of the sound source.

A method of providing a parametric minimum audible angle for a capability of auditory spatial positioning, including the steps of:

classifying spatial positions to identify those with a highest correct rate and those with a lowest correct rate on the basis of a result of testing a subject's capability of spatial positioning;

selecting a random spatial point in the spatial positions with the highest correct rate and the lowest correct rate as an initial point of a sound source;

reducing a spatial distance between sound sources equal-proportionally between an edge point of an area and the initial point;

enabling, by a speed control module of a servo motor driver, a timeframe for movement from one to any other sound source point to be consistent; and matching a spatial position selected by the subject to the spatial position of the sound source in real-time, keeping reducing the minimum audible angle if the matching is correct, and taking an audible angle greater than or equal to a threshold as the minimum audible angle for the subject.

In a specific implementation, if the matching is incorrect, five sets of spatial position points are randomly updated near the current position on the basis of the current audible angle, and the matching is tried again.

The reduction of the spatial distance between the sound sources concerns specifically changes of a horizontal angle, a vertical angle, and a distance between sphere centers.

The technical solution provided by the invention is advantageous in the following aspects.

1. The sound source spatial positioning and test system is highly intelligent and parametric; the invention uses an industrial personal computer as the main control hardware device of the parametric test system, which can randomly generate a data sequence of the spatial positions of the test points on a spatial sphere on the basis of clinical data and physiological parameters of the subject through an algorithm, cache the generated coordinate data of the spatial points to a data list (data stack) according to time labels, and transmit the data to a movement control system by following a communication protocol.

2. The circumferential movement of the test system is driven by a servo motor and a gear structure, and accurate position control (pulse number check) is achieved through real-time communication and feedback to calibrate with the industrial personal computer; in addition, groove-shaped tracks are used, apart from reducing friction during circumferential movement and other interferences, to play a protective role and improve the safety factor of the parametric test system.

3. The radial movement of the test system is driven by a servo motor and a screw structure. The movement pulse number of the spatial radial control motor is calculated by the industrial personal computer and sent to the servo motor driver, and then a position control method is used to achieve the precise radial movement position control. Moreover, in conjunction with the screw structure, the accuracy of the radial movement of the parametric test system is improved, and circular movement of the servo motor is converted into linear movement.

4. The vertical movement of the test system is driven by a servo motor and a roller structure. The vertical movement pulse data of the industrial personal computer are sent to the vertical movement servo motor driver, and a length of a reverse chain is accurately controlled through the position control method. After this, the roller structure functions, which doubles the accuracy of the control of the length of the reverse chain, so that the accuracy requirement of the vertical movement can be achieved.

5. Through the position control of the movement control system (an axial movement servo motor and a gear set, a radial movement servo motor and a screw set, the vertical servo motor and the roller structure), precise control on the spatial sphere can be realized, reaching a high accuracy up to 0.05°.

6. The three-dimensional display system uses two 144 Hz monitors. One of them serves as the display for the operator, which displays the changes in the three-dimensional space of the position of the sound source in real time, so that the operator can observe the position of the sound source in real-time; the other serves as the display for the subject, and the subject can rotate, zoom and translate a three-dimensional model of the sphere space of the sound source as he/she wants with a mouse, and click on the monitor to identify the position of the sound source spatially.
7. A medical index test subsystem for testing the subject's auditory deviation angle is used. The subsystem compares the list of coordinates of the generated sound source points with the sound source position points selected by the subject, calculates a correct rate and gives an average value of the deviation angles, which serve as the basis for the operator (doctor) to make an objective evaluation.
8. A parametric test of the minimum audible angle is done, where a point in the auditory three-dimensional space is selected as the initial point, and another point around it is selected as the final point. Between the two points, the distance from the sound source point to the center of the sphere is reduced in proportion, the control mode of the servo motor driver for circumferential movement, radial movement and vertical movement is adjusted to a speed control mode, so that a timeframe for the movement from one to any other sound source point is consistent. The distance of the sound source point keeps changing until the subject cannot correctly identify the spatial position of the sound source point, at which time, the test ends and the spatial angle between the two sound source points is the minimum audible angle for the subject.
9. In addition to identifying the spatial angle of the sound source, the invention also allows the subject to identify the distance between the sound source and the center of the sphere, which is significantly different from the sound cage (with only the spatial angle identification, but no spatial distance identification).
10. This test system can create a sound source at any fixed point within the range of a three-dimensional sphere through circumferential movement, radial movement and vertical movement depending on clinical needs of a doctor and requires only one sound source generator.

DETAILED DESCRIPTION OF THE PRESENT INVENTION

To further clarify the objects, technical solutions, and advantages of the present invention, the embodiments of the invention will be described in detail below.

Embodiment 1

Figure 1:
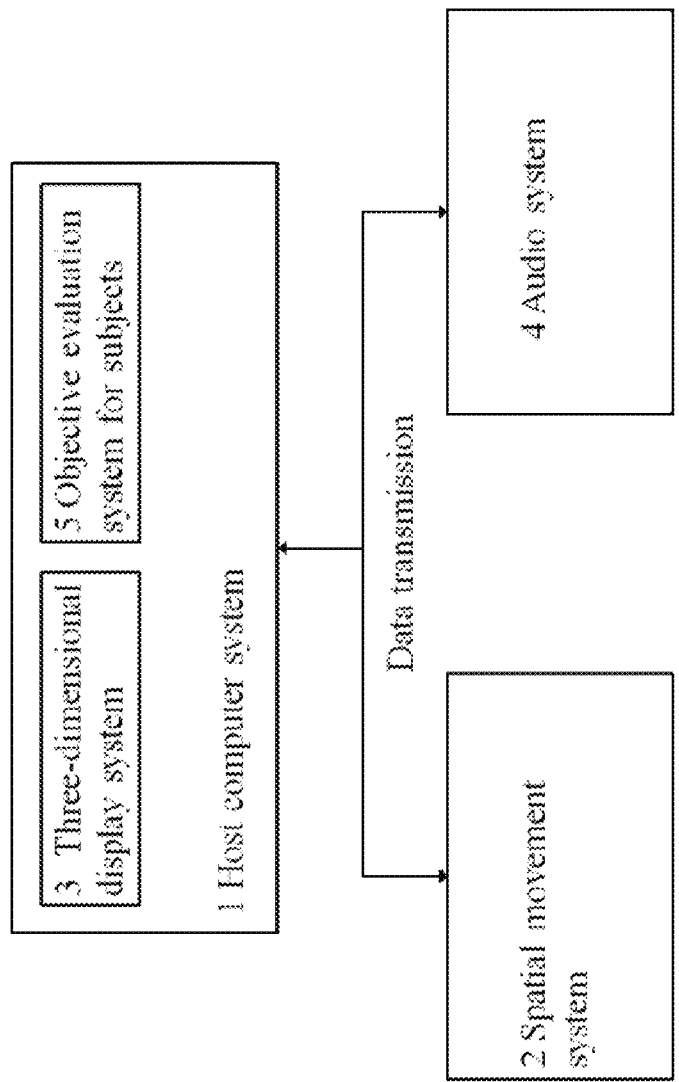
FIG. 1 is a structural diagram of a parametric system for testing a capability of auditory spatial positioning.
Figure 2:
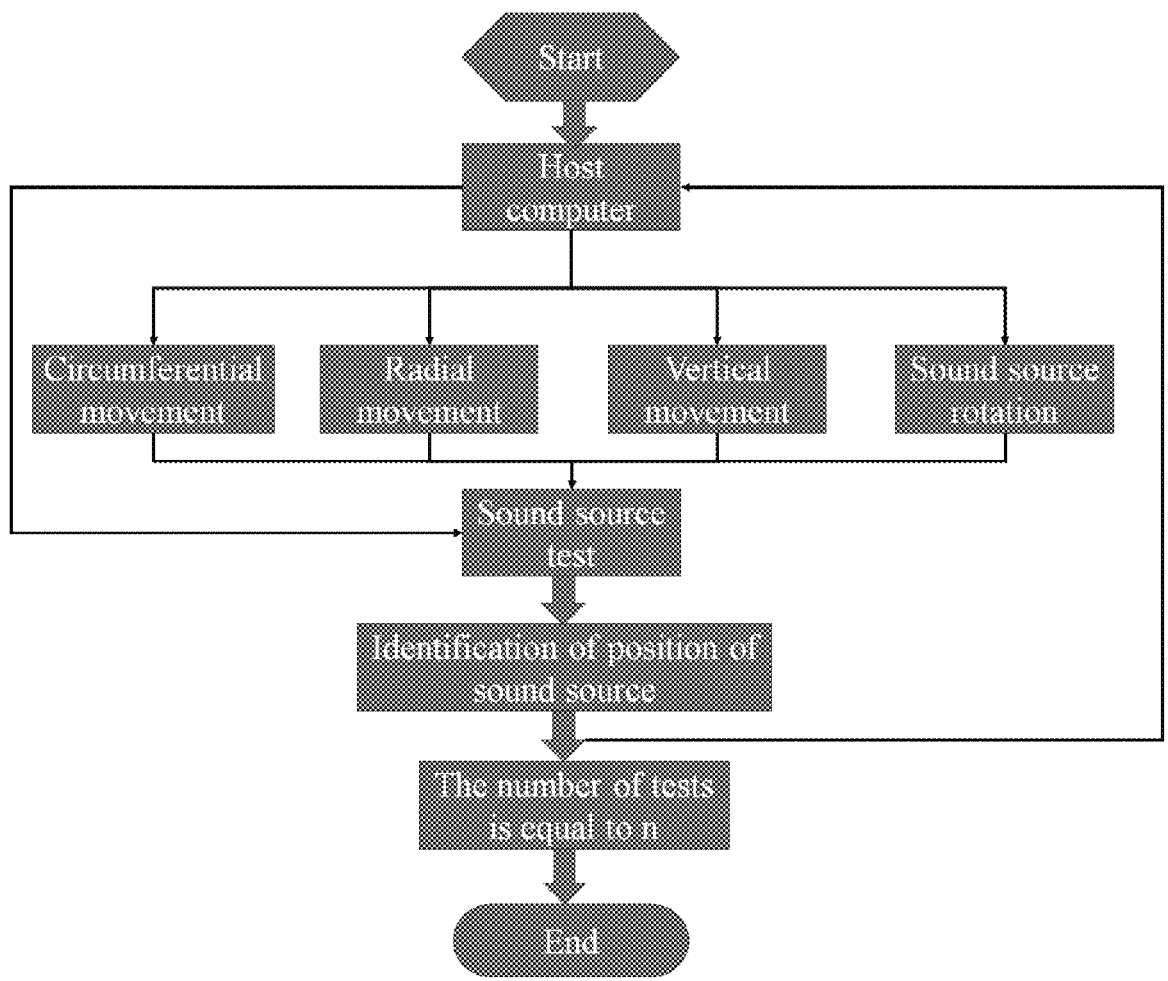
FIG. 2 is a working flow chart of the parametric system for testing a capability of auditory spatial positioning.

A parametric system for testing a capability of auditory spatial positioning is shown in FIGS. 1, 2, the parametric system includes: a host computer system 1, a spatial movement system 2, a real-time three-dimensional display system 3, an audio system 4, and an objective evaluation system for subjects 5, wherein:

the host computer system 1 calculated spatial movement data according to a spatial coordinate conversion algorithm based on nonlinear least squares and communicate with a slave computer (a driver and a controller of a servo motor); the spatial movement system 2 realized precise control of any spatial position through circumferential movement, radial movement and vertical movement;

the real-time three-dimensional display system 3 was built into the host computer system 1 to reconstruct a three-dimensional model in real time through a system image and feedback real-time movement data of the system on the basis of virtual reality technologies, and the audio system 4 randomly generated a type of audio data of a sound source and a sound source with equal-difference decibels; and the objective evaluation system for subjects 5 tested the spatial positioning of the sound source by human ears, selected spatial point data, matched to real spatial data of the sound source, and provided an objective evaluation.

In a specific implementation, the host computer system 1 was composed of an industrial personal computer, a monitor with a 144 Hz refresh rate, and communication cables. The industrial personal computer randomly generated a time series and spatial positions of spatial test points of the sound source according to the spatial conversion algorithm on the basis of clinical indicators and physiological parameters of the subjects, cached such data in a data area (cache list, stack), and sent the data to a driver of the spatial movement system 2 by following a communication protocol; the monitor with a 144 Hz refresh rate provided a virtual three-dimensional display based on the real environment.

The spatial movement system 2 was composed of three sub-modules, i.e., an axial movement sub-module, a radial movement sub-module and a vertical movement sub-module. The movement of each sub-module, through the corresponding servo motor driver, controlled the accuracy of the movement. The servo motor driver communicated with the industrial personal computer in real-time through the communication cable by following a communication protocol, so that the precise positioning of the sound source at any point within the spatial sphere was realized.

The real-time three-dimensional display system 3 was a data information processing part, the pulse data sent by the servo motor driver of each sub-module was subjected to a conversion rule to adjust spatial positions of all sub-components in a virtual model (for example, circumferential movement system, radial movement system, etc.) in a world coordinate system, to reconstruct a three-dimensional data display system and present it on the monitor.

Wherein, the above conversion rule provided that the parameters of the servo motor correspond one-to-one to the communication protocol, thereby improving the position accuracy, which will not be described in detail in the embodiment of the invention.

The audio system randomly generated optimal sound source audio data in a same number as that of spatial positions on the basis of clinical experience (usually an expert library, not shown in this embodiment of the invention) and the physiological parameters of the subjects and matched the sound source audio data randomly one by one to spatial coordinate data, and the generated audio signals were randomly and repeatedly played according to a time sequence of coordinate points, rendering the test result more objective.

According to the objective evaluation system for subjects 5, a spatial position of the sound source was selected by a subject on an interface of the real-time three-dimensional display system 3, the spatial position selected by the subject is tried to match a spatial position in a cache list, and then the objective evaluation system for subjects 5 provided an objective evaluation result of the subject's capability of spatial positioning.

Embodiment 2

With reference specific steps, the technical solution in Embodiment 1 will be further explained as following:

- 101: Spatial positions were classified to identify those with a highest correct rate and those with a lowest correct rate on the basis of a result of testing a subject's capability of spatial positioning.
- 102: A random spatial point was selected from the spatial positions with the highest correct rate and the lowest correct rate as an initial point of a sound source;
- 103: A spatial distance between sound sources was reduced equal-proportionally between an edge point of an area and the initial point, including changes of a horizontal angle, a vertical angle, and a distance between sphere centers.

In a specific implementation, a line connecting the initial point and the center of the sphere was taken as an axis, and an area having an included angle of 10° in relation to the axis and intersecting the sphere spatially was an alternative area.

- 104: A speed control module of a servo motor driver was used to enable a timeframe for movement from one to any other sound source point to be consistent (to prevent the subject from predicting the next spatial position of the spatial sound source in advance based on experience).
- 105: A spatial position selected by the subject was matched in real-time to the spatial position of the sound source, the minimum audible angle continued to reduce if the matching was correct; if the matching is incorrect, five sets of spatial position points are randomly updated near the current position on the basis of the current audible angle; if the matching correct rate is greater than or equal to a threshold (for example, 80%), the test continues, otherwise the test ends, and a current audible angle value is taken as the minimum audible angle for the subject.

Wherein, the above-mentioned threshold, i.e., 80%, is set as per practical applications, which is not limited in the embodiment of the invention.

Embodiment 3

- 201: An operator inputted the physiological parameters of the subject and the number of tests to an interactive interface of the industrial personal computer, and the industrial personal computer randomly generated a coordinate sequence of spatial points and caches it in the data list.
- 202: The industrial personal computer arranged coordinates in a data list in such a manner that a spatial mid-point between the subject's ears as a current coordinate origin, converted the coordinates into circumferential movement pulses, radial movement pulses and vertical movement pulses, and temporarily stored these data in a data stack according to a time label.
- 203: The data frames in the data stack were transmitted to the servo motor driver through a data cable by following communication protocol RS-485 according to the principle of "first in, first out".
- 204: The data will be sent to the servo motor driver with a corresponding address number in an order of circumferential movement firstly, then radial movement, and finally vertical movement. After the circumferential movement was completed, the radial movement started, and then the vertical movement followed. When the three movements were completed, the movement of the spatial position of the sound source ends.
- 205: A set of audios were selected from a test audio library as the sound source audio data, and the sound source data were played for three times at equal intervals at each spatial position, this was the basis for the subject to identify positions with his/her ears spatially.
- 206: The subject identified the spatial position according to audio information of the sound source and selected the spatial position of a virtual entity on the subject's monitor, the industrial personal computer matched coordinate information of the spatial position selected by the subject with cache data of a corresponding spatial position in sequence and provided a result whether the subject had correctly identified the spatial position of the sound source.
- 207: Steps 204 through 206 were repeated and a counter is started, and the test is stopped when the number of tests reaches a preset number (the ratio of the number of high-frequency, intermediate-frequency, and low-frequency audios is guaranteed to be 1:1:1 during each test). After the test, based on the subject's performance of identification, a correct rate of the subject was provided.

Embodiment 4

- 301: According to the test results of the subject's spatial positioning capability, the space was divided into eight parts, namely, left front upper, left front lower, left rear upper, left rear lower, right front upper, right front lower, right rear upper, and right rear lower parts; and according to the subject's performance of identification, the spatial positions of the highest correct rate and the lowest correct rate were recorded.
- 302: A spatial point was selected from the spatial positions with the highest correct rate and those with the lowest correct rate, respectively, as the initial point of the sound source test of the minimum audible angle;
- 303: A spatial distance between sound sources was reduced equal-proportionally between an edge point of an area and the initial point, including changes of a horizontal angle, a vertical angle, and a distance between sphere centers; test spatial sound source position points were generated randomly in equidistant small spatial spheres, the three-dimensional coordinates of the spatial sound source points were placed in the data list in the order of time labels; the entire minimum audible angle test included three parts, i.e., a test of the minimum audible angle for sound source movement in a horizontal plane, a test of the minimum audible angle for sound source movement in a mid-plane, and a test of the minimum audible angle for sound source movement in an auditory space, that is, the sound source moved in a selected plane or space according to a certain rule, and an objective evaluation was provided based on the subject's performance of identification;

304: the data in the data list were converted into the number of pulses of circumferential movement, radial movement and vertical movement, and were sent to a receiving end of the servo motor driver through the communication cable by following protocol RS-485. A speed control module of a servo motor driver was used to enable a timeframe for movement from one to any other sound source point to be consistent (to prevent the subject from predicting the next spatial position of the spatial sound source in advance based on experience).

Figure 3:
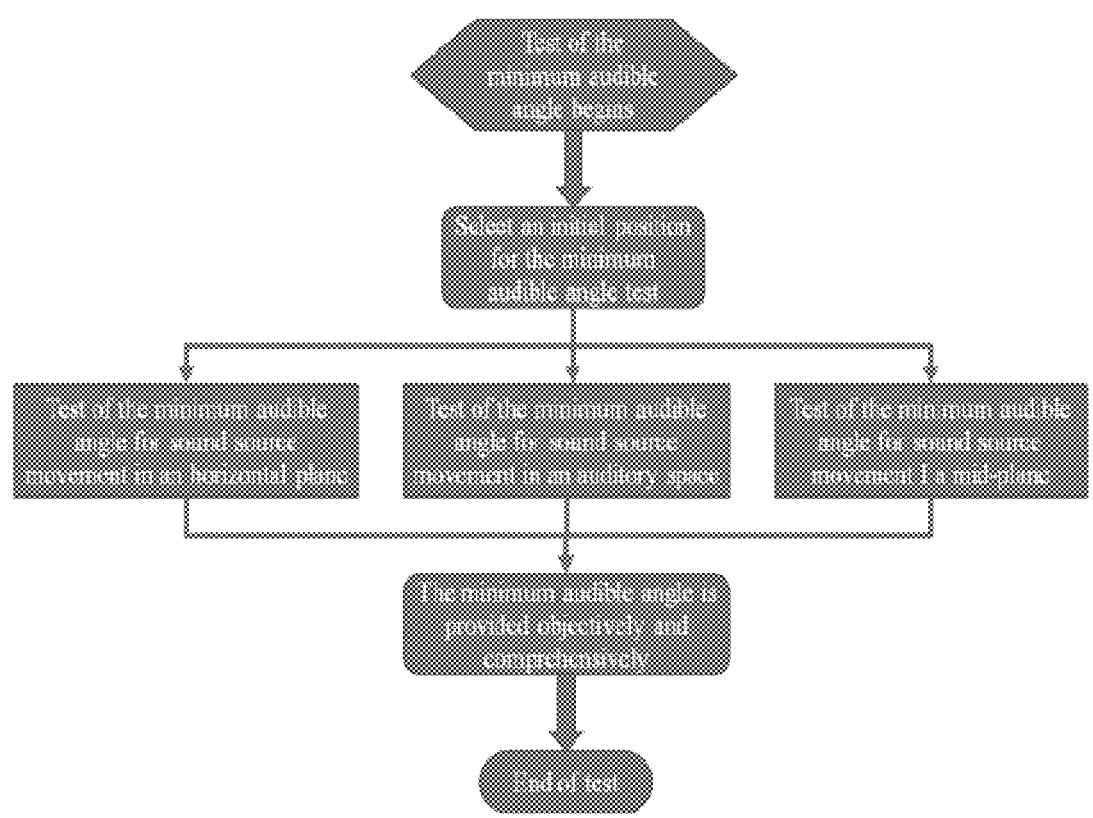
FIG. 3 is a working flow chart of an auditory minimum audible angle test.

305: A spatial position selected by the subject was matched in real-time to the spatial position of the sound source, the minimum audible angle continued to reduce if the matching is correct; if the matching is incorrect, five sets of spatial position points are randomly updated near the current position on the basis of the current audible angle; if the matching correct rate is greater than or equal to 80%, the test continues, otherwise the test ends, and a current audible angle value was taken as the minimum audible angle for the subject. The entire flow chart is shown in FIG. 3.

In the embodiments of the invention, the model of each device is not limited unless otherwise indicated, and the model of other devices is not limited as long as the device can complete the above-mentioned functions.

Those skilled in the art can understand that the accompanying drawings are only schematic diagrams of a preferred embodiment, and the serial numbers of the above-mentioned examples of the invention are only for illustrative purposes, and do not represent the superiority or inferiority of the embodiments.

The above is only the preferred embodiment of the invention and is not intended to limit the invention. Any modification, equivalent replacement, improvement, etc. made within the spirit and principle of the invention shall be included in the scope of the invention.

What is claimed is:

1. A parametric system for testing a capability of auditory spatial positioning, comprising:
   a host computer system, calculating spatial movement data according to a spatial coordinate conversion algorithm based on nonlinear least squares and communicating with a slave computer;
   a spatial movement system, realizing precise control of any spatial position through circumferential movement, radial movement and vertical movement;
   a real-time three-dimensional display system, built into the host computer system to reconstruct a three-dimensional model in real time through a system image and feedback real-time movement data of the system on the basis of virtual reality technologies;
   an audio system, randomly generating a type of audio data of a sound source and a sound source with equal-difference decibels; and
   an objective evaluation system for subjects, testing the spatial positioning of the sound source by human ears, selecting spatial point data, matching to real spatial data of the sound source, and providing an objective evaluation.

2. The parametric system for testing a capability of auditory spatial positioning according to claim 1, wherein the host computer system is composed of an industrial personal computer, a monitor with a 144 Hz refresh-rate, and a communication cable;
   wherein the industrial personal computer randomly generates a time series and spatial positions of spatial test points of the sound source according to the spatial conversion algorithm on the basis of clinical indicators and physiological parameters of the subjects, caches such data in a data area, and sends the data to a driver of the spatial movement system by following a communication protocol.

3. The parametric system for testing a capability of auditory spatial positioning according to claim 2, wherein the industrial personal computer arranges coordinates in a data list in such a manner that a spatial mid-point between the subject's ears as a current coordinate origin, converts the coordinates into circumferential movement pulses, radial movement pulses and vertical movement pulses, and temporarily stores these data in a data stack according to a time label.

4. The parametric system for testing a capability of auditory spatial positioning according to claim 3, wherein the subject identifies the spatial position according to audio information of the sound source and selects the spatial position of a virtual entity on the subject's monitor, the industrial personal computer matches coordinate information of the spatial position selected by the subject with cache data of a corresponding spatial position in sequence, and provides a result whether the subject has correctly identified the spatial position of the sound source.

5. The parametric system for testing a capability of auditory spatial positioning according to claim 1, wherein the audio system randomly generates optimal sound source audio data in a same number as that of spatial positions on the basis of clinical experience and the physiological parameters of the subjects and matches the sound source audio data randomly one by one to spatial coordinate data, and generated audio signals are randomly and repeatedly played according to a time sequence of coordinate points.

6. The parametric system for testing a capability of auditory spatial positioning according to claim 1, wherein according to the objective evaluation system for subjects, a spatial position of the sound source is selected by a subject on an interface of the real-time three-dimensional display system, the spatial position selected by the subject is tried to match a spatial position in a cache list, and then the objective evaluation system for subjects provides an objective evaluation result of the subject's capability of spatial positioning.

7. A method of providing a parametric minimum audible angle for a capability of auditory spatial positioning, comprising the steps of:
   classifying spatial positions to identify those with a highest correct rate and those with a lowest correct rate on the basis of a result of testing a subject's capability of spatial positioning;
   selecting a random spatial point in the spatial positions with the highest correct rate and the lowest correct rate as an initial point of a sound source;
   reducing a spatial distance between sound sources equal-proportionally between an edge point of an area and the initial point;
   enabling, by a speed control module of a servo motor driver, a timeframe for movement from one to any other sound source point to be consistent; and
   matching a spatial position selected by the subject to the spatial position of the sound source, keeping reducing the minimum audible angle if the matching is correct, and taking an audible angle greater than or equal to a threshold as the minimum audible angle for the subject.

8. The method of providing a parametric minimum audible angle for a capability of auditory spatial positioning according to claim 7, wherein if the matching is incorrect, five sets of spatial position points are randomly updated near the current position on the basis of the current audible angle, and the matching is tried again.

9. The method of providing a parametric minimum audible angle for a capability of auditory spatial positioning according to claim 7, wherein the reduction of the spatial distance between the sound sources concerns specifically changes of a horizontal angle, a vertical angle, and a distance between sphere centers.

\* \* \* \* \*